_(12)_ United States Patent [19]
Bender et al.

[11] Patent Number: 5,998,638
[45] Date of Patent: Dec. 7, 1999

[54] ESTER SALT OF 5α-PREGN-16-EN-3β-OL-20-ONE 3-SULFATE

[75] Inventors: Reinhold H. W. Bender, Valley Forge, Pa.; Mahdi B. Fawzi, Morristown, N.J.; Horace Fletcher, III, Pottstown, Pa.; George O. Morton, Hillsdale; Syed M. Shah, East Hanover, both of N.J.; Xuejun Tang, New City, N.Y.

[73] Assignee: American Home Products Corporation, Madison, N.J.

[21] Appl. No.: 09/063,581

[22] Filed: Apr. 21, 1998

Related U.S. Application Data

[60] Provisional application No. 60/046,818, May 2, 1997.

[51] Int. Cl.$^6$ .............................. A61K 31/57; C07J 7/00
[52] U.S. Cl. ........................................ 552/599; 514/182
[58] Field of Search .............................. 552/599; 514/182

[56] References Cited

U.S. PATENT DOCUMENTS

| | | | |
|---|---|---|---|
| 2,834,712 | 5/1958 | Beall et al. | 167/74.5 |
| 3,608,077 | 9/1971 | Ginsig | 424/243 |
| 3,952,031 | 4/1976 | Phillipps et al. | 260/397.45 |
| 4,154,820 | 5/1979 | Simoons | 424/175 |

OTHER PUBLICATIONS

Schindler et al., Biol. Neonate, 27(3–4), 192–207 (abstract), 1975.

Gustafsson, J. A., Eur. J. Biochem., 14(3), 560–6, 1970.

Physicians' Desk Reference, 48th edition, 2594–6, 1994.

Baillie, T.A. et al., J Ster Biochem, Identification and Quantitation of 16α–Hydroxy–$C_{21}$ Steroid Sulphates in Plasma from Pregnant Women, 1976, 7, pp. 203–209.

Bolger, M.B. et al., Pharm Res, In vitro and In vivo Activity of 16,17–dehydro–epipreg–nanolones:17,20–Bond Torsional Energy Analysis and D–ring Conformation,. 13(10), 1996.

Neher, R. et al., Steroids, Isolating, Identifying and Synthesizing a New Steroid from Adrenal Glands, 155th report, 1958, 1667–1692.

Gyermek, L. et al., J. Med. Chem., 11(1), Jan. 1968, pp. 117–125.

Phillipps, G. H., J. Ster. Biochem., 6(5), May 1975, pp. 607–613.

Im, W. B. et al., Mol. Pharmaco., 37(3), Mar. 1990, pp. 429–434.

Smith, H. E. et al., J. Biol. Chem., 249(18), Sep. 25, 1974, pp. 5924–5932.

_Primary Examiner_—Phyllis G. Spivack
_Attorney, Agent, or Firm_—Arnold S. Milowsky

[57] ABSTRACT

This invention provides a pharmaceutically acceptable salt of 5α-pregn-16-3β-ol-20-one 3-sulfate ester, which is useful as a progestational agent.

3 Claims, No Drawings

ESTER SALT OF 5α-PREGN-16-EN-3β-OL-20-ONE 3-SULFATE

BACKGROUND OF THE INVENTION

This application claims the benefit of U.S. Provisional Application No. 60/046,818, filed May 2, 1997.

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17-β-estradiol, dihydroequilenin and 17-β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris(hydroxymethyl)aminomethane (TRIS) to prevent hydrolysis is discussed in U.S. Pat. No. 4,154,820.

One of the compounds described herein, 5α-pregn-16-en-3β-ol-20-one 3-sulfate ester sodium salt is a minor component of PREMARIN (conjugated equine estrogens).

DESCRIPTION OF THE INVENTION

In accordance with this invention, there is provided a pharmaceutically acceptable salt of 5α-pregn-16-en-362-ol-20-one 3-sulfate ester which is useful as a progestational agent. The structure of 5α-pregn-16-en-3β-ol-20-one is shown as compound (1) in Scheme I.

Pharmaceutically acceptable salts of 5α-pregn-16en-3β-ol-20-one 3-sulfate ester include, but are not limited to, the alkali metal salts, alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group.

As 5α-pregn-16-en-3β-ol-20-one 3-sulfate ester sodium salt is a minor component of PREMARIN (conjugated equine estrogens), this invention also provides 5α-pregn-16-en-3β-ol-20-one 3-sulfate ester sodium salt in greater than 1 percent purity.

This invention also provides a compound consisting essentially of 5α-pregn-16-en-3β-ol-20-one 3-sulfate ester sodium salt, and a compound consisting essentially of a pharmaceutically acceptable salt of 5α-pregn-16-en-3β-ol-20-one 3-sulfate ester.

This invention further provides a method of using 5α-pregn-16-en-3β-ol-20-one or a pharmaceutically acceptable salt of its 3-sulfate ester as a progestational agent.

The compounds of this invention can be prepared from readily available starting materials according to the processes in Scheme I, as shown for 5a-pregn-16-en-3β-ol-20-one 3-sulfate ester sodium salt.

For example, according to Scheme I, 5α-pregn-16-en-3β-ol-20-one (1) [P. L. Julian et al., J. Am. Chem. Soc. 72, 5145 (1950)] was treated with one or more equivalents of triethylamine:sulfur trioxide reagent in a suitable solvent such as tetrahydrofuran at room temperature to afford 5α-pregn-16-en-3β-ol-20-3-sulfate, triethylammonium salt (2a). The triethylammonium salt (2a) was treated with aqueous sodium hydroxide to afford 5a-pregn-16-en-3β-ol-20-one-3-sulfate, sodium salt (2b).

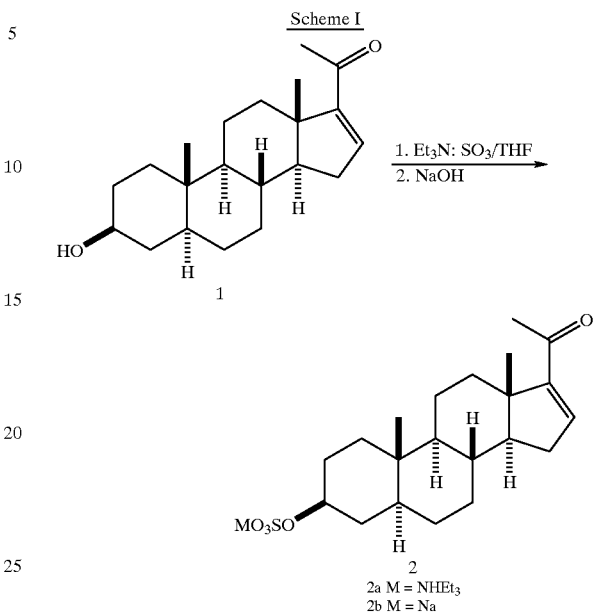

Scheme I

The compounds of this invention are progestational agents, and are therefore useful as oral contraceptives (male and female), in hormone replacement therapy (particularly when combined with an estrogen), in the treatment of endometriosis luteal phase defects, benign breast and prostatic diseases and prostatic and endometrial cancers. The compounds of this invention are also useful in protecting against epileptic seizures, in cognition enhancement, in treating Alzheimer's disease, dementias, vasomotor symptoms related to menopause, and other central nervous system disorders The compounds of this invention are further useful in stimulating erythropoiesis.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 μg/kg–750 μg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following provides the preparation of representative compounds of this invention.

EXAMPLE 1

5α-Pregn-16-en-3β-ol-20-one-3-sulfate, triethylammonium salt (2a)

5α-Pregn-16-en-3β-ol-20-one (2.0 g, 6.32 mmol) was dissolved in 50 ml of tetrahydrofuran. Sulfur trioxide triethylamine complex (1.2 g, 6.6 mmol) was added. The mixture was stirred at room temperature for 20 hours. After addition of 50 ml of ether, the precipitate was collected on a Buchner funnel, washed with ether and dried; 2.4g (76%).

$^1$H NMR (300Mhz, DMSO-$d_6$)

δ 0.78 (s, 3H), 0.80 (s, 3H), 1.19 (t, 9H), 2.21 (s, 3H), 3.10 (q, 6H), 3.92 (m, 1H), 6.87 (t, 1H), 8.80 (bs, 1H)

m/z (ES negative) 395(M-H)

5α-Pregn-16-en-3β-ol-20-one 3-sulfate ester sodium salt (2b)

Crude triethylammonium salt (2a) was stirred in 1N sodium hydroxide at room temperature for 48 hours. The precipitate was collected on a Buchner funnel, washed with water and dried; 2.8g (85%).

$^1$H NMR (300Mhz, DMSO-$d_6$)

δ 0.78 (s, 3H), 0.80 (s, 3H), 2.20 (s, 3H), 3.92 (m, 1H), 6.87 (t, 1H)

m/z (ES negative) 395(M-H)

What is claimed is:

1. 5α-Pregn-16-en-3β-ol-20-one 3-sulfate ester sodium salt, which is at least 1 percent pure.

2. A compound which consists essentially of a pharmaceutically acceptable salt of 5α-pregn-16-en-3β-20-one 3-sulfate ester, wherein the pharmaceutically acceptable salt of the 3-sulfate ester is an alkali metal salt, alkaline earth metal salt, ammonium salt, alkylammonium salt containing 1–6 carbon atoms, or dialkylammonium salt containing 1–6, carbon atoms in each alkyl group, or trialkylammonium salt containing 1–6 carbon atoms in each alkyl group.

3. A compound which consists essentially of 5α-pregn-16-en-3β-ol-20-one 3-sulfate ester sodium salt.

* * * * *